United States Patent [19]
Stenberg et al.

[11] 4,332,476
[45] Jun. 1, 1982

[54] METHOD AND APPARATUS FOR STUDYING SURFACE PROPERTIES

[76] Inventors: Johan E. Stenberg, Hedelundsragën 5, S-41743 Göteborg; Lars B. Stiblert, Övre Besvärsgatan 4, S-411 29 Göteborg; Erland T. Sandström, Jungmansgaton 53, S-413 11 Göteborg, all of Sweden

[21] Appl. No.: 140,881

[22] Filed: Apr. 16, 1980

[30] Foreign Application Priority Data

Apr. 17, 1979 [SE] Sweden .................. 7903311

[51] Int. Cl.³ .................. G01N 21/21; G01J 4/00
[52] U.S. Cl. .................. 356/369; 350/394
[58] Field of Search .................. 356/364–370, 356/445, 448, 322, 327; 250/225; 350/152, 157, 394

[56] References Cited

U.S. PATENT DOCUMENTS

| | | | |
|---|---|---|---|
| 3,622,245 | 11/1971 | Rasmussen | 356/365 |
| 3,893,749 | 7/1975 | Ferray | 350/157 |
| 4,105,338 | 8/1978 | Kuroha | 356/369 |

OTHER PUBLICATIONS

Azzam, R. M. A., "Two Reflection Null Ellipsometer Without a Compensator", Jr. of Physics E Scientific Instruments, vol. 9, #7, 1976, pp. 569–572.

Neal et al., "Ellipsometry & its Applications to Surface Examination", Jr. of Physics E Scientific Instruments, vol. #5, 1973, pp. 409–416.

Zaghloul, A. R. M., "Modified O'Bryan Ellipsometer (MOE) for Film-Substrate Systems", Optics Communications, 10-1978, pp. 1–3.

*Primary Examiner*—William H. Punter
*Attorney, Agent, or Firm*—Fleit & Jacobson

[57] ABSTRACT

In a method and apparatus for studying surface properties of a testpiece, such as refractive index or thickness of a layer or film on said surface, electromagnetic radiation is directed on to the test surface or a reference surface which has known properties, and reflected on to the other surface. The angle of incidence in respect of the incident radiation, in relation to the respective surfaces, are the same, and the surfaces are so arranged that when the radiation is reflected from one surface on to the other, the parallel polarization component of the first reflection is the perpendicular component of the second reflection. Radiation in the same state of polarization as before the first reflection is extinguished by an analyzer, providing for point-to-point comparison between the two surfaces.

19 Claims, 9 Drawing Figures

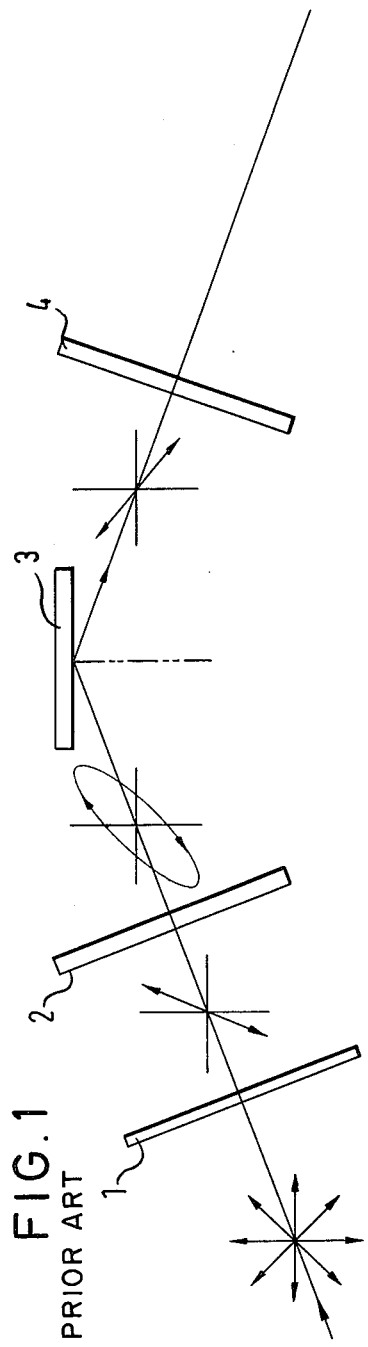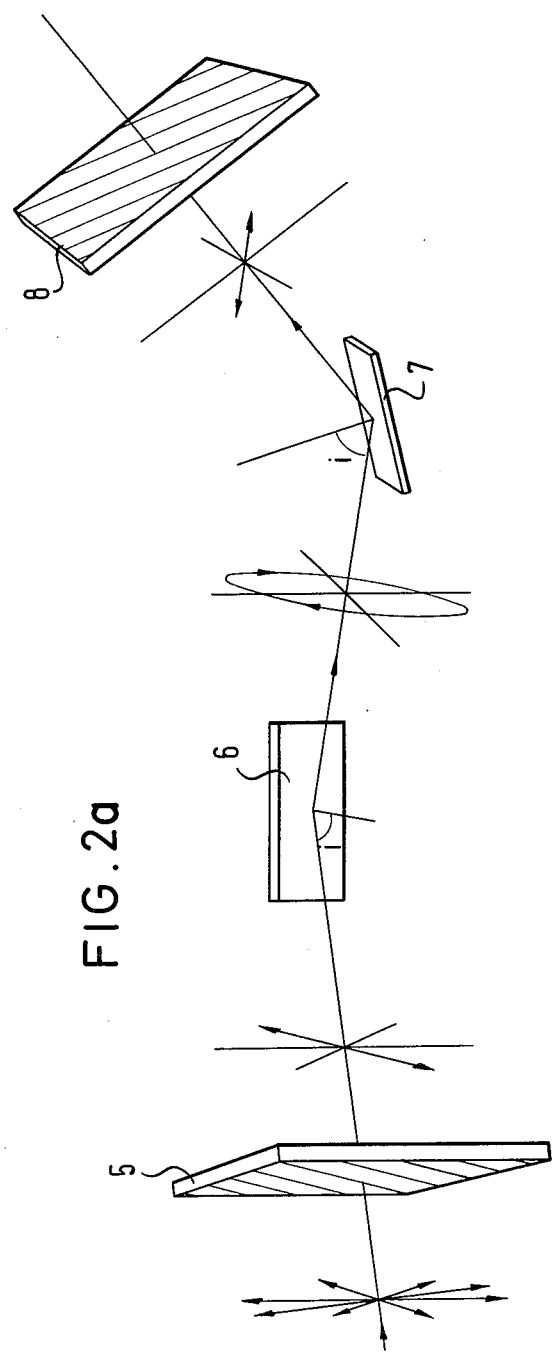
FIG. 1 PRIOR ART
FIG. 2a

METHOD AND APPARATUS FOR STUDYING SURFACE PROPERTIES

BACKGROUND OF THE INVENTION

This invention is concerned generally with a method and apparatus for studying the surface properties of a sample or testpiece, for example the refractive index or the thickness of a layer or film on the surface, using electromagnetic radiation which is reflected at the surface to be studied, with reflected, linearly polarised radiation being extinguished by an analyzer.

Ellipsometer instruments have been proposed for determining the optical properties of sample or testpiece surfaces, which operate on the principle that parallel monochromatic light falls on the surface through a polarizer which provides for linear polarization of the light. The light then passes through a compensator which produces a phase difference between the polarization components of the light, thus producing elliptical polarization of the light. After reflection of the light at the surface of the testpiece, the light is analyzed and calculation makes it possible to achieve information about the quality and nature of the surface at which the light was reflected.

If the surface of the sample or testpiece serves as the substrate for a dielectric film, the reflection properties of that surface are influenced. From this, it is possible to calculate the thickness and the refractive index of the film, if the optical constants of the substrate are known. The degree of accuracy in determining thickness and refractive index vary according to the nature of the substrate, the angle of incidence and the thickness of the film. If the substrate comprises silicon, and if the angle of incidence of the radiation on the sample or testpiece is 70°, the thickness of the film may be determined with an accuracy of measurement of ±0.05 nm.

However, when measuring the thickness of thin films, it is necessary for the thickness to be known to approximately half the wavelength of the radiation, as the setting or adjustment angles of the polarizer and the analyzer are periodically repeated; if there is no approximate reference point or criterion in regard to measuring the thickness of the film, before the measuring operation is performed, difficulties can occur as the correct values must be selected from a number of differing values. In this respect, besides the data determined with the ellipsometer, it is also necessary to have additional information which makes it possible to decide which is the correct thickness value within a multiplet of a plurality of measurement values.

Therefore, an ellipsometer of such a design is only capable of limited use. Although the ellipsometer is relatively simple in design, the measuring operation turns out to be relatively complicated, particularly because the measurement values must be determined in dependence on polarizer and analyzer settings, and because, after the measuring operation, extensive calculations are still required in order to arrive at the actual measurement values.

Also known are automatic ellipsometers which have servo and computer equipment which carry out the manual calculation work. However, ellipsometers of this kind are expensive and complicated pieces of equipment.

SUMMARY OF THE INVENTION

An object of the present invention is to provide a method and apparatus for studying the surface properties of a test sample, which are of greater simplicity than the prior art.

Another object of the invention is to provide an ellipsometer instrument which permits direct study of the physical properties of a surface, using not only white light but also ultra-violet and infra-red.

Another object of the invention is to provide an ellipsometry method which involves point-to-point comparison between two surfaces, a test surface to be measured and a reference surface with known properties.

A still further object of the invention is to provide a novel ellipsometry instrument which is fast and convenient to use and which is particularly suitable for routine measurement or production control.

These and other objects are achieved by an ellipsometry method for studying the physical properties of the surface of a testpiece or sample, such as a layer or film on a surface thereof, by means of electromagnetic radiation which is reflected at said surface, with polarized radiation after reflection being extinguished by an analyzer. The radiation is additionally reflected at a reference surface which has known properties, with the same angle of incidence as at the surface of the testpiece or sample, so that the polarization component or direction of the radiation reflected at one said reflecting surface, which component or direction is parallel to the plane of incidence at said one surface, is caused to be perpendicular to the plane of incidence at the other reflecting surface, and the portion of radiation which is in the same polarization condition as before the first reflection at one of the two surfaces is extinguished by the analyzer.

In an apparatus for studying the properties of the surface of a testpiece or sample, by means of electromagnetic radiation such as white light, which is reflected at the surface, there is a polarizer which is arranged in the direction of radiation upstream of the testpiece or sample, to produce polarized radiation, and an analyzer which is arranged downstream of the testpiece or sample in the direction of radiation, to extinguish the polarized radiation reflected by the testpiece or sample. Disposed between the polarizer and the analyzer, in addition to the testpiece or sample, is a reference surface with known properties, in such a way that the radiation is reflected from one surface to the other, the angles of incidence of the radiation at the two surfaces are the same, and the polarization component or direction of the radiation reflected at one of the surfaces, which component or direction is parallel to the plane of incidence at the one surface, is perpendicular to the plane of incidence at the other surface.

In the invention therefore, the polarized radiation is reflected both at a reference surface and also at the test surface, the radiation impinging on both surfaces at the same angle of incidence. In this case, the reflected radiation of one surface is directed on to the other surface. This is effected in such a way that the polarization component or the direction of deflection of the part of the radiation which is reflected from one surface on to the other, which component or direction is parallel to the plane of incidence at the reflecting surface, is perpendicular to the plane of incidence at the other reflecting surface. The condition of polarization of the radiation after reflection at the second surface is analyzed by means of an analyzer, by the part of the radiation which is in the same polarization condition as the radiation directed on to the first reflecting surface being extinguished.

BRIEF DESCRIPTION OF THE DRAWINGS

FIG. 1 is a diagrammatic view of a known kind of ellipsometer,

FIG. 2a shows an embodiment of the present invention,

DESCRIPTION OF THE PREFERRED EMBODIMENTS

Figure 2B:
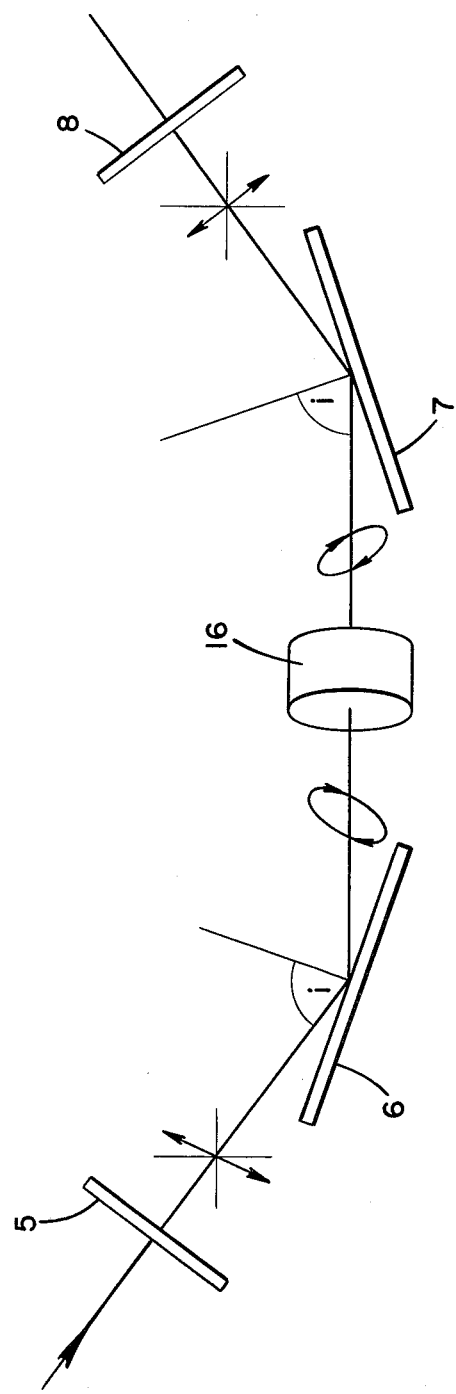
FIG. 2b shows a further embodiment of the present invention.

In order to enhance full comprehension of the present invention, reference will first be made to FIG. 1 which shows a diagrammatic view of a conventional ellipsometer wherein parallel monochromatic light strikes against a polarizer 1 which produces linearly polarized light, at a desired angle. The linearly polarized light passes through a compensator which is in the form of a quarterwave plate 2; the plate 2 is so set that polarized light, at an angle ±45°, is retarded by a quarter of the wavelength, in comparison with polarized light at an angle of −45°. The angles are measured from the plane of incidence and go positive in a counter-clockwise direction when viewing the light source. The light leaving the compensator 2 has undergone elliptical polarization and impinges on a test surface 3. The test surface 3 reflects the components which are normal to the plane of incidence, and the components parallel thereto, with a different time retardation effect and intensity. Upon reflection, the phase difference can be compensated by the light being linearly polarized again after reflection. An analyzer 4 disposed downstream of the test surface 3 can be so set that this linearly polarized light is then extinguished. The angular setting of the analyzer 4 then provides information regarding the change in intensity or strength during reflection. The angular setting of the polarizer 1 gives information about the change in phase of the light upon reflection. Joint evaluation of the values of the angular settings of the polarizer 1 and the analyzer 4 makes it possible to calculate given optical properties of the test surface 3, for example the refractive index or the attenuation at metal surfaces.

The thickness of a thin dielectric film on the test surface can be determined by limitations in respect of the measuring area, on the assumption that the optical constants of the test surface are known.

Reference will now be made to FIG. 2a which shows an apparatus embodying the principles of the present invention, showing that, in contrast to the known ellipsometer, the compensator 2 of FIG. 1, in the form of the quarterwave plate, has been replaced by an additional reflecting reference surface 6. In addition, with the apparatus shown herein, radiation within a given wavelength range, for example white light, can be used. In the embodiment illustrated, the incident parallel beam is polarized at −45° by means of a polarizer 5. Thereafter, the radiation, for example visible light, impinges against the reference surface 6 and is reflected thereby. The light reflected by the reference surface 6 is polarized elliptically, depending on the nature of the reference surface 6. Reference numeral 7 in FIG. 2a denotes a test surface which is of the same material as the reference surface 6 and which is so arranged that the light impinges on the test surface 7 at the same angle of incidence i as the angle of incidence of the light on the reference surface 6. In the embodiment illustrated, however, the plane of incidence at the test surface 7 is perpendicular to the plane of incidence at the reference surface 6. If the reference surface 6 and the test surface 7 are identical, the two components of the polarized light are reflected at the same reflection angles. This means that the light reflected by the test surface 7 is linearly polarized again. This polarized light is passed through an analyzer 8 whose polarization direction is perpendicular to the polarization direction of the polarizer 5. Therefore, in the analyzer 8, the proportion of light in which the optical reflection properties of the reference surface 6 and the test surface 7 are identical is extinguished. If the radiation used is white light or if the radiation is within a given wavelength range, total extinction in respect of all wavelengths occurs if the two surfaces are identical.

The method may be improved and facilitated in its performance if for example the reference surface 6 is of such a nature that the optical properties thereof vary in a known manner. In that case, the apparatus also provides corresponding information in regard to the test surface 7, with respect to different optical properties thereof.

The apparatus of the invention as illustrated in FIG. 2a does not use a compensator in the form for example of a quarter-wave plate. This means that the radiation does not have to be monochromatic, and radiation within a given wavelength range, for example white light, may be used. This gives rise to substantial advantages with regard to measuring the thickness of thin films. If for this purpose the reference surface 6 is covered with a film of known uniform thickness, or if the thickness of the film is varied in known manner, then, when studying the test surface, for example when using a photographic recording, a black band or line is obtained at the position of the projected pattern of the test surface, at which the thickness of the layer on the test surface is the same as the thickness of the known layer on the reference surface. If, when the films on the test surface and the reference surface vary in thickness, the films are identical to each other, a corresponding number of black bands or lights are to be found on the photograph.

Coloured bands or lines appear on both sides of the black band or line which is the indication in regard to the corresponding thicknesses of the films, depending on the extinction of the individual wavelength components of the white light. Distinguishing the black band or line from the coloured bands may be easily done. When using monochromatic light, which must be used when employing the known ellipsometry procedures, a plurality of black bands occur, and it is necessary to use special additional evaluation procedures in order to determine which of the plurality of black bands produced, corresponds to the film thickness to be determined.

The invention therefore makes it possible for the test surface 7 to be studied directly, thereby making the measuring procedure substantially easier. If for example the surface 6 has a known layer whose thickness varies in one direction, for example linearly, then variations in thickness can be studied and detected along the test surface 7, for example by means of an eyepiece. A photograph for example of this can be taken, producing a curve which shows the thickness of the film or layer as a function for example of the distance from a given starting point, along the test surface.

The measuring procedure is further facilitated by the fact that the polarizer 5 and the analyzer 8 do not have to be movable.

The possibility of directly studying the test surface also provides the necessary condition required for analyzing surfaces, for example for comparing different surface alloys.

As will be appreciated, FIG. 2a shows a simple system embodying the principles of the invention. As indicated in FIG. 2b, it is also possible however for an optical means 16, for example a prism, which turns the direction of polarization of the light through 90° between the reference surface 6 and the test surface 7, to be disposed between the two surfaces 6 and 7. This arrangement makes it possible for the beam to extend in the same plane, for example in the same plane of incidence. By using a total-reflection prism, for example, the beam can be caused to extend in such a way that the reference surface 6 and the test surface 7 can be disposed in the same plane, and can be arranged for example on a table. This arrangement is also advantageous when both surfaces comprise fluid surfaces. A compact assembly may also be attained by using this kind of system.

The mode of operation of the system of the invention is not bound to the wavelength of the radiation. In this respect, this can be utilised for ellipsometric spectroscopy. This can be effected by the wavelength being altered along one side of the test surface 7, thus giving a direct representation of the manner in which the surface properties are dependent on wavelength. This is advantageous in particular when studying the absorption in a thin layer which includes a dye or colouring agent.

It will be readily appreciated that the invention is not restricted to using the visible light wavelength range, for electromagnetic radiation of other wavelengths can also be used. For that purpose, the system will then include additional means whereby the radiation is converted into visible light, depending on the nature and/or the wavelength of the radiation. For example, image-converting means may be used for converting infrared radiation into visible light.

The invention makes it possible for the reflection properties for two surfaces for electromagnetic radiation to be compared together. This makes it possible to study and measure physical properties of a test surface, this being effected by comparison with a reference surface which has known physical surface properties. The method and system of the invention thus make use of the recognition that, for isotropic surfaces which are not optically active, two polarization components (parallel and perpendicular to the plane of incidence) of the light are reflected independently of each other.

Figure 3:
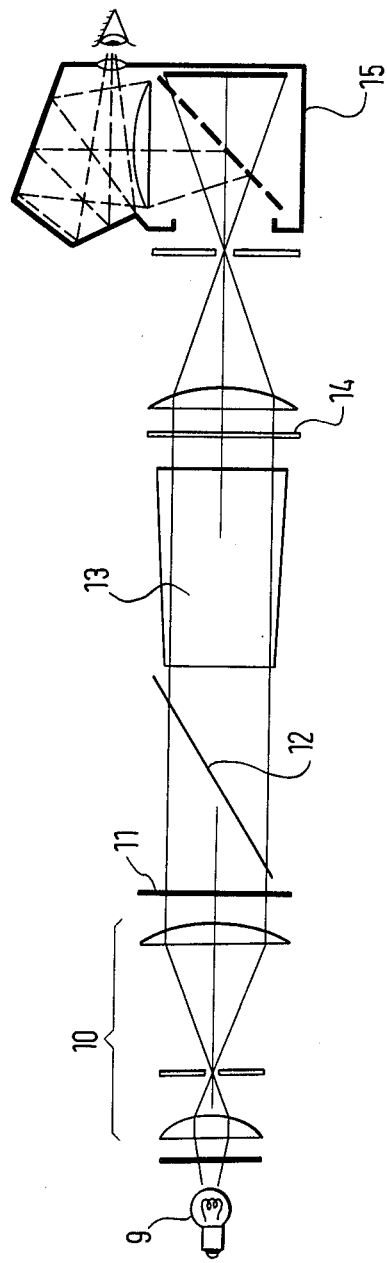
FIG. 3 shows a test set-up.
Figure 4:
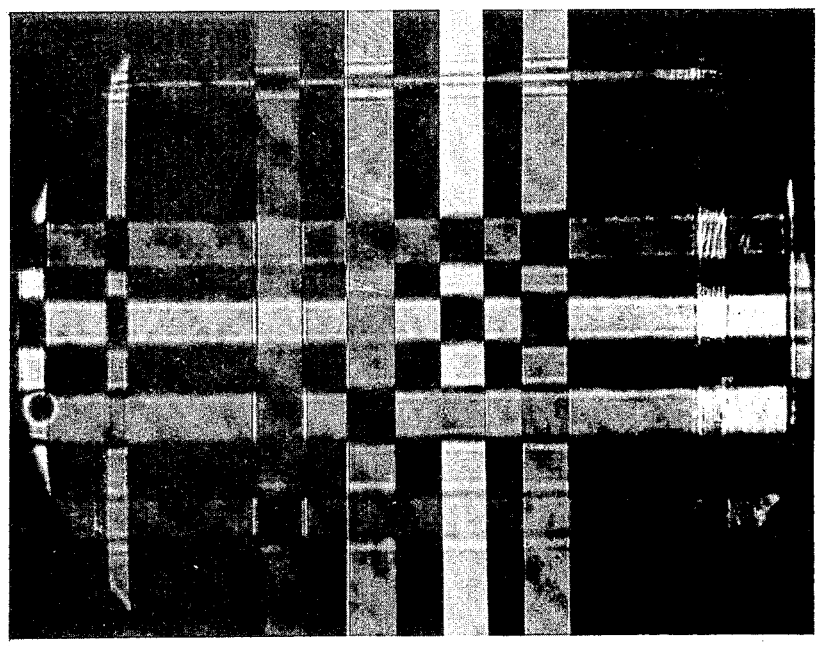
FIG. 4 shows a photograph of a testpiece or sample on which different metal layers are applied.

FIG. 3 is a diagrammatic view of a test arrangement which, as viewed in the direction of the beam, comprises a lamp 9, a collimator 10, a polarizer 11, a reference surface 12, a test surface 13, an analyzer 14 and a camera 15. A test arrangement of this kind was used to carry out analysis of a metal surface, the result of which is shown in FIG. 4. For the purposes of carrying out the test, a gold film of 100 nm thickness was evaporated or vapour-deposited on a microscope slide. Silver, aluminium, chromium and nickel strips were then evaporated on to the surface film using a suitable masking technique, so that the strips were evenly spaced from each other. It was impossible to distinguish between the silver and aluminium strips or between the chromium and the nickel strips, using the naked eye.

Using the test arrangement shown in FIG. 3, it was possible to produce the photograph shown in FIG. 4 wherein the gold layer appears as a black background, with silver, aluminium, chromium and nickel strips being clearly recognisable in the drawing, moving upwardly and rightwards. The same results can be obtained with alloys with similar properties.

Figure 5A:
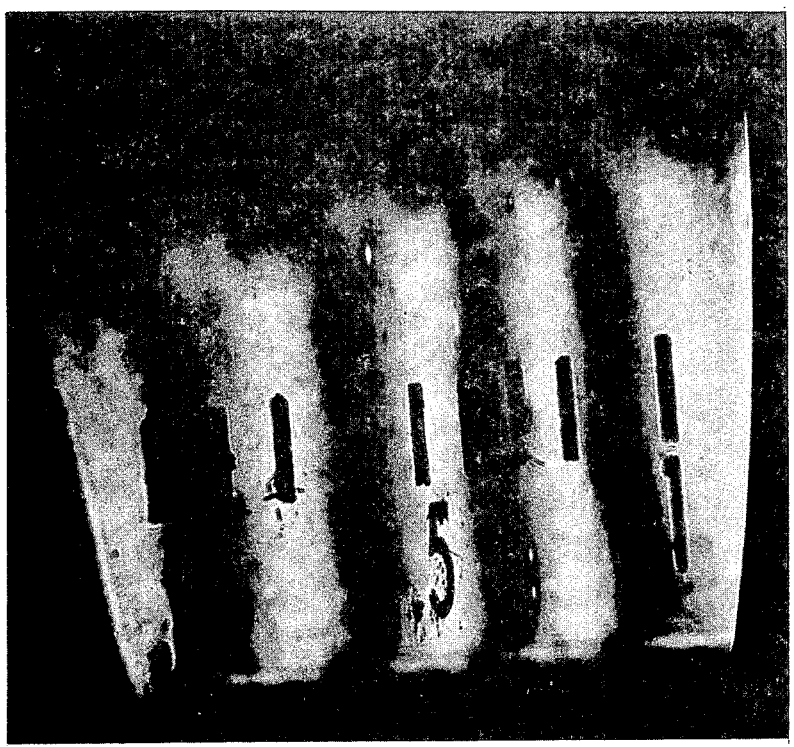
FIG. 5a shows a photograph of measurement results using a ellipsometer.
Figure 5B:
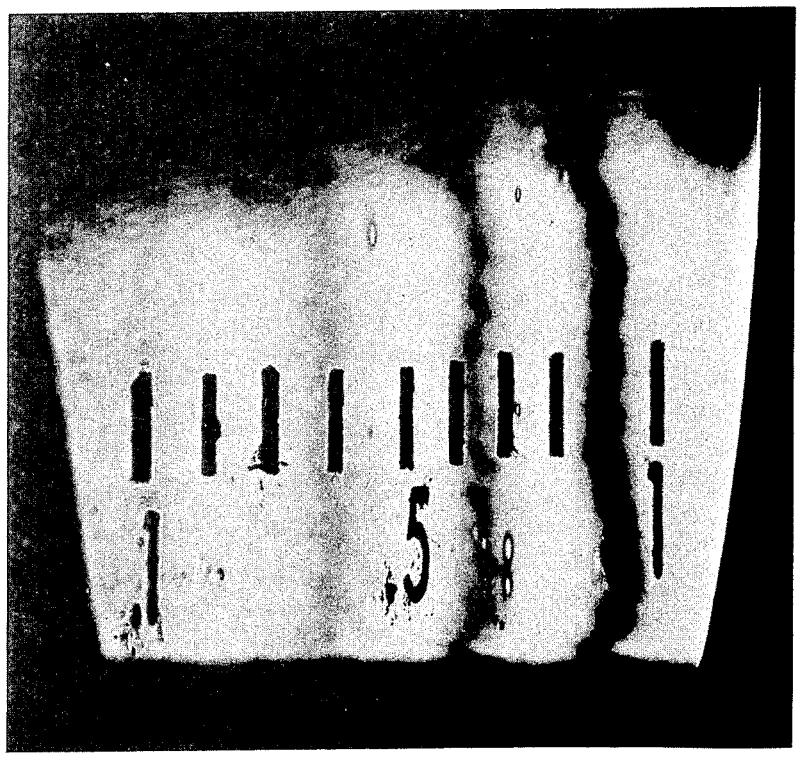
FIG. 5b shows a photograph of a test result in determining the thickness of a film, using an embodiment in accordance with the invention.

FIGS. 5a and 5b show results obtained in measuring the thicknesses of $SiO_2$ films. The reference surface used was a 1 μm thick $SiO_2$ film on a silicon substrate. FIG. 5a shows the measuring results obtained with a ellipsometer, using monochromatic light. As FIG. 5a clearly shows, the result obtained is four bands or lines, of which one represents the actual measurement in respect of the thickness of the film. Therefore, additional evaluation procedures must be carried out, in order to arrive at the actual film thickness.

Figure 6:
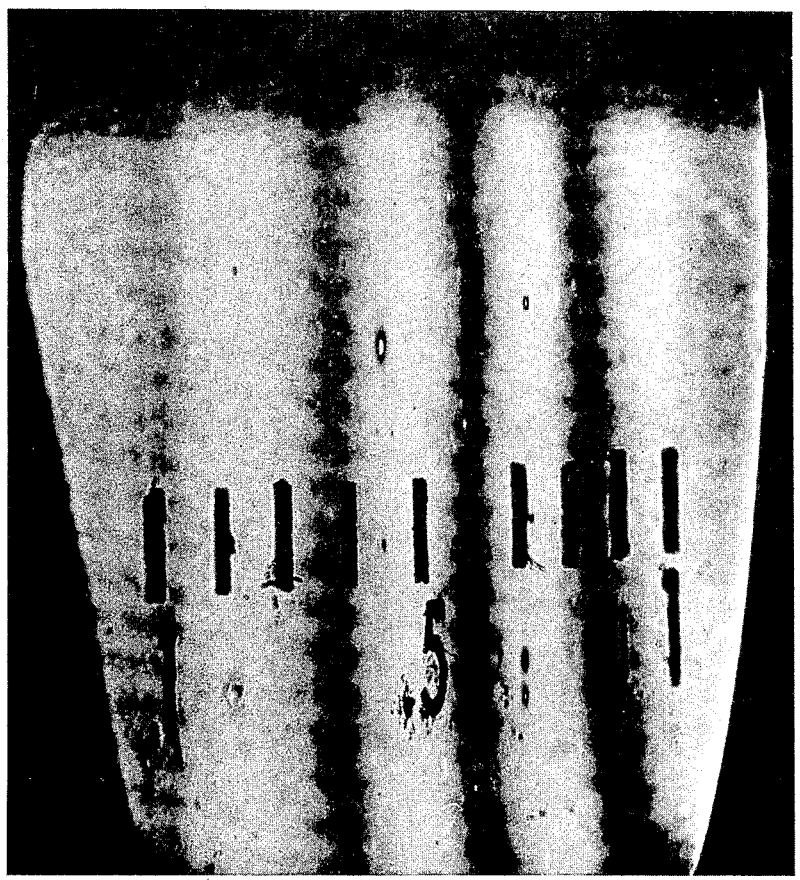
FIG. 6 shows a further example of use of the invention.

In contrast, as shown in FIG. 5b, using the invention directly produces a band or line which represents the measurement in respect of the film thickness. Thus, a direct reading may be obtained by using a suitable scale. Extinction of the light, or the black band or line, occurs when the reference surface and the test surface have the same refractive index. It has been found however that the thickness of organic films with a refractive index of about 1.50 can be measured by means of an $SiO_2$ film as a reference surface with a refractive index of about 1.46. FIG. 6 shows that the thickness of thin films of photoresist can be measured by means of an $SiO_2$ film as the reference surface.

Figure 7:
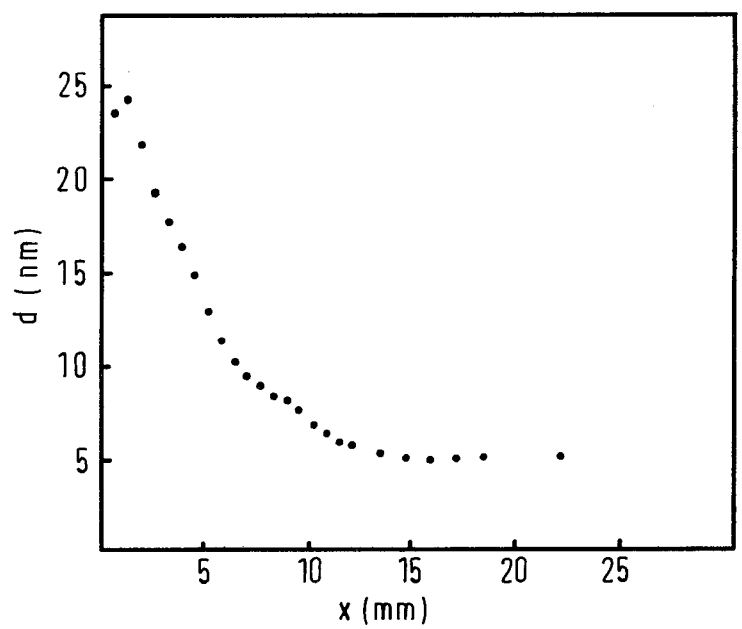
FIG. 7 shows measurement results in respect of a thickness profile, in an immunobiological reaction, wherein the upper curve was measured by means of a conventional ellipsometer and the lower curve was measured by means of an ellipsometer in accordance with the invention.
Figure 7:
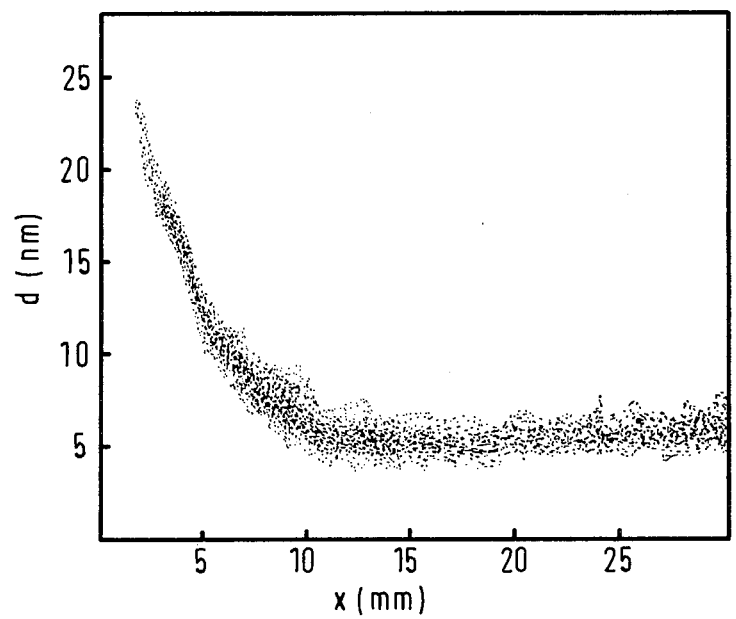

FIG. 7 shows two curves in respect of a profile obtained in an immunobiological reaction. The upper curve was obtained by means of a conventional ellipsometer, a measuring time of about 5 minutes being required for each point on the curve. A total period of about 2 hours was required in order to produce the entire curve. The lower curve in FIG. 7 was produced by means of the invention (comparison ellipsometer) and can be recorded by a camera, that is to say, the profile can be directly determined by means of the invention. The comparison or reference surface was an $SiO_2$ film whose thickness varied linearly from 2 to 25 nm along a distance of 20 mm. This means that even organic monomolecular layers can be studied.

The present invention makes it possible to effect direct study of the physical surface properties, by obtaining from the test surface an image in which the regions whose properties are the same as those of the reference surface appear dark. The tests may be carried out not only in the white light range but also in the ultraviolet and infra-red ranges. Use in ellipsometrical spectroscopy is also possible. The spectrum of use is wide and ranges from immunobiological tests to surface tests in semiconductor manufacture.

It will be seen therefore that the system of the present invention provides a point-to-point comparison between a test surface to be measured and a reference surface with known properties, so that, depending on the properties of the reference surface, different measurements can be performed. The system is very convenient to use and very rapid, and is particularly suitable for carrying out routine-type measurements or production control operations. The system has no moving parts, and a pocket-size model would also be a practical proposition.

Various modifications may be made in the invention as described above, without thereby departing from the spirit and scope thereof.

What is claimed is:

1. In a method of studying physical properties of a testpiece surface to obtain a direct point-to-point comparison between the testpiece surface and a reference surface having known properties, said method comprising the steps of:
   (a) transmitting electromagnetic radiation toward the testpiece surface to be studied;
   (b) polarizing said electromagnetic radiation prior to its reaching said testpiece surface to produce polarized radiation;
   (c) reflecting said polarized electromagnetic radiation from said testpiece surface so as to produce polarized reflected radiation; and
   (d) analyzing said polarized reflected radiation so as to extinguish said polarized reflected radiation;
   the improvement comprising the additional reflecting step, between steps (b) and (d), of additionally reflecting said polarized radiation at said reference surface having known surface properties, thereby providing further polarization;
   wherein said reflecting step (c) and said additional reflecting step comprises reflecting at the same angle of incidence;
   wherein said reflecting step (c) and said additional reflecting step are accomplished by respective reflecting surfaces, and wherein the radiation reflected at one of said respective reflecting surfaces has a polarization component which, being parallel to the plane of incidence at one surface, is perpendicular to the plane of incidence at the other of said respective reflecting surfaces;
   wherein said additional reflecting step enables said direct point-to-point comparison between the reference surface and the testpiece surface to be made, while at the same time providing phase-shift compensation, by means of said further polarization; and
   wherein said analyzing step (d) comprises extinguishing radiation of the same state of polarization as exists before the first one of said reflecting step (c) and said additional reflecting step to be executed.

2. A method as set forth in claim 1 wherein the radiation used is linearly polarized during said step (b).

3. A method as set forth in claim 1 wherein the radiation used is in a given frequency range.

4. A method as set forth in claim 3 wherein said radiation is white light.

5. A method as set forth in claim 1 wherein the wavelength of said radiation is altered.

6. A method as set forth in claim 1 wherein said polarized radiation comprises linearly polarized radiation, said linearly polarized radiation being directed onto the reference surface, and wherein said additional reflecting step produces elliptically polarized radiation, said elliptically polarized radiation being directed onto the testpiece surface.

7. A method as set forth in claim 1 wherein the surface properties of the reference surface are varied.

8. Apparatus for studying surface properties of a testpiece surface by means of electromagnetic radiation to obtain a direct point-to-point comparison between the testpiece surface and a reference surface having known properties, said apparatus comprising:
   radiation source means for generating radiation along a radiation beam path toward a testpiece,
   polarizing means disposed in the radiation beam path upstream of the testpiece for receiving and polarizing said radiation to produce a polarized radiation beam,
   said testpiece having a testpiece surface for receiving and reflecting said polarized radiation beam, and
   analyzing means disposed in the radiation beam path downstream of the testpiece for extinguishing polarized radiation in said polarized radiation beam reflected by the testpiece,
   said apparatus further comprising reference means having a reference surface with known properties, disposed between the polarizing means and the analyzing means, for receiving and reflecting said polarized radiation beam, thereby providing further polarization;
   wherein the angles of incidence of the radiation at said reference surface and said testpiece surface are at least substantially identical, and wherein the polarized radiation beam reflected at one of said reference surface and said testpiece surface has a polarization direction which, being parallel to the plane of incidence at said one surface, is perpendicular to the plane of incidence at the other of said reference surface and said testpiece surface; and
   wherein said reference means enables said direct point-to-point comparison between the reference surface and the testpiece surface to be made while at the same time providing phase-shift compensation, by means of said further polarization.

9. Apparatus as set forth in claim 8 including rotating means for rotating the direction of polarization of the radiation reflected from said one surface to the other of said reference surface and said testpiece surface.

10. Apparatus as set forth in claim 9 wherein the direction of polarization is rotated 90° so that the radiation beam is in the same plane of incidence at said reference surface and said testpiece surface.

11. Apparatus as set forth in claim 8 wherein the planes of incidence of said reference surface and said testpiece surface are perpendicular to each other.

12. Apparatus as set forth in claim 8 wherein said polarizing means and said analyzing means are fixedly set.

13. Apparatus as set forth in claim 8 wherein the reference surface has different surface properties.

14. Apparatus as set forth in claim 13 wherein said different surface properties are with respect to the composition thereof.

15. Apparatus as set forth in claim 13 wherein said different surface properties are with respect to the thickness of a film on said surface.

16. Apparatus as set forth in claim 8 wherein said radiation source means produces a parallel beam of said radiation, said polarizing means produces linearly polarized light, said reference surface is disposed downstream of said polarizing means, said testpiece is disposed downstream of said reference surface, and said analyzer means is disposed downstream of said testpiece, and wherein radiation reflected by the reference surface is elliptically polarized, and is directed onto the testpiece surface, and wherein the testpiece surface reflects linearly polarized radiation which is directed to the analyzing means.

17. Apparatus as set forth in claim 8 wherein linearly polarized radiation is directed onto a first one of the testpiece and reference surfaces.

18. An ellipsometer for obtaining a direct point-to-point comparison between a test surface and a reference surface having known properties, said ellipsometer comprising:
  electromagnetic radiation source means for generating radiation along a radiation beam path;
  means for holding said test surface;
  analyzing means disposed downstream of the test surface holding means, relative to the radiation beam path, for receiving and analyzing said radiation generated along said radiation beam path; and
  means for holding said reference surface having known surface properties, disposed between the radiation source and the analyzing means, wherein the radiation is reflected first from one of said test and reference surfaces to generate a first reflection which is polarized and has a parallel polarization component, and then from the other of said test and reference surfaces to generate a second reflection which is further polarized and has a perpendicular polarization component, and wherein the parallel polarization component of the first reflection is the perpendicular component of the second reflection;
  wherein generation of said second reflection which is further polarized enables said direct point-to-point comparison between the reference surface and the test surface to be made, while at the same time providing phase-shift compensation, by means of said generation of said second reflection which is further polarized.

19. A method of studying physical properties of a test surface to obtain a direct point-to-point comparison between a test surface and a reference surface having known properties, comprising the steps of:
  (a) transmitting electromagnetic radiation;
  (b) directing said radiation onto a first one of a test surface and a reference surface which has known properties to develop a first reflection beam which is polarized and has a parallel polarization component; and
  (c) directing said radiation beam onto a second one of said test surface and said reference surface to develop a second reflection beam which is further polarized and has a perpendicular component;
  wherein said radiation beam is directed onto each of said test and reference surfaces at the same angle of incidence, and wherein the parallel polarization component of the first reflection is the perpendicular component of the second reflection, and wherein radiation in a state of polarization as exists before step (b) is extinguished;
  wherein development of said second reflection beam which is further polarized enables said direct point-to-point comparison between the reference surface and the test surface to be made, while at the same time providing phase-shift compensation, by means of said generation of said second reflection beam which is further polarized.

* * * * *